United States Patent [19]

Schwartz

[11] Patent Number: 4,713,218
[45] Date of Patent: Dec. 15, 1987

[54] TUBE TRAP APPARATUS

[75] Inventor: Henry L. Schwartz, Los Gatos, Calif.

[73] Assignee: Sequoia-Turner Corporation, Mountain View, Calif.

[21] Appl. No.: 757,646

[22] Filed: Jul. 22, 1985

[51] Int. Cl.⁴ ............................................. G01N 37/00
[52] U.S. Cl. ...................................... 422/99; 141/165; 141/177; 141/312; 141/372; 422/63; 422/100
[58] Field of Search .............. 141/165, 177, 312, 372; 73/864.14, 864.25, 864.24; 422/63, 99, 100, 102, 104

[56] References Cited

U.S. PATENT DOCUMENTS

| | | | |
|---|---|---|---|
| 775,307 | 11/1904 | Ortmann | 141/165 |
| 1,444,540 | 2/1923 | Freedman | 141/165 |
| 3,879,987 | 4/1975 | Yasuhiro et al. | 141/165 |
| 4,040,556 | 8/1977 | Dahle | 227/120 |
| 4,058,370 | 11/1977 | Suovaniemi | 422/100 |
| 4,539,852 | 9/1985 | Jacobs | 422/100 |

Primary Examiner—Michael S. Marcus
Attorney, Agent, or Firm—Limbach, Limbach & Sutton

[57] ABSTRACT

A tube restraining apparatus is described for centering the mouth of a loosely held test tube prior to the insertion of a probe. The apparatus is automatically activated by a motor driven carriage and the cooperation of the probe and the bail. The mouth of the tube is centered by contacting the tube rim with the conical inner surface of the restrainer.

9 Claims, 6 Drawing Figures

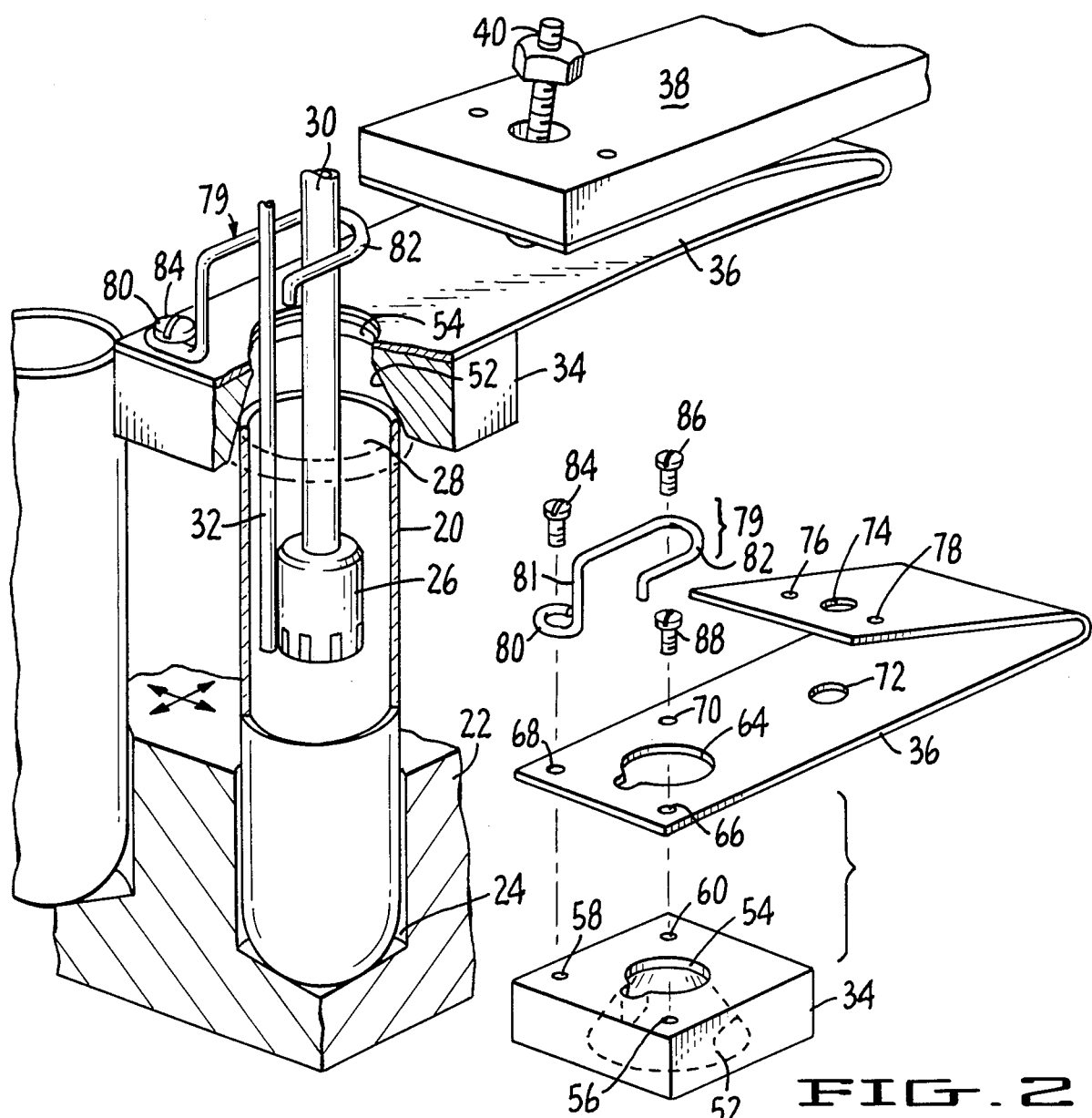
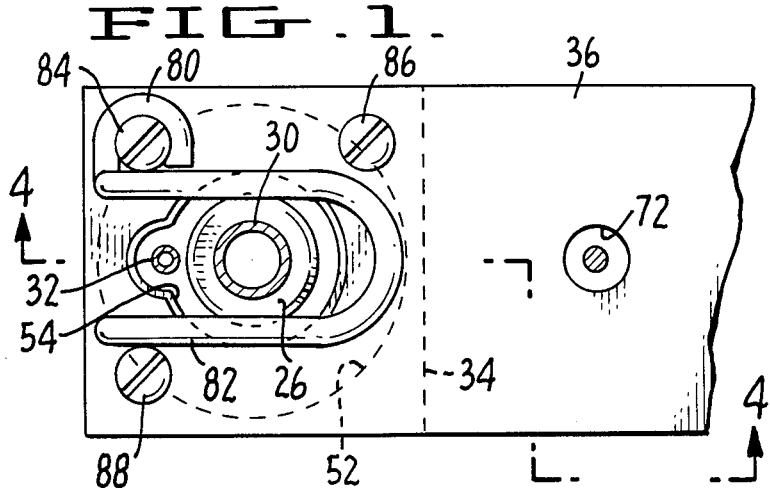

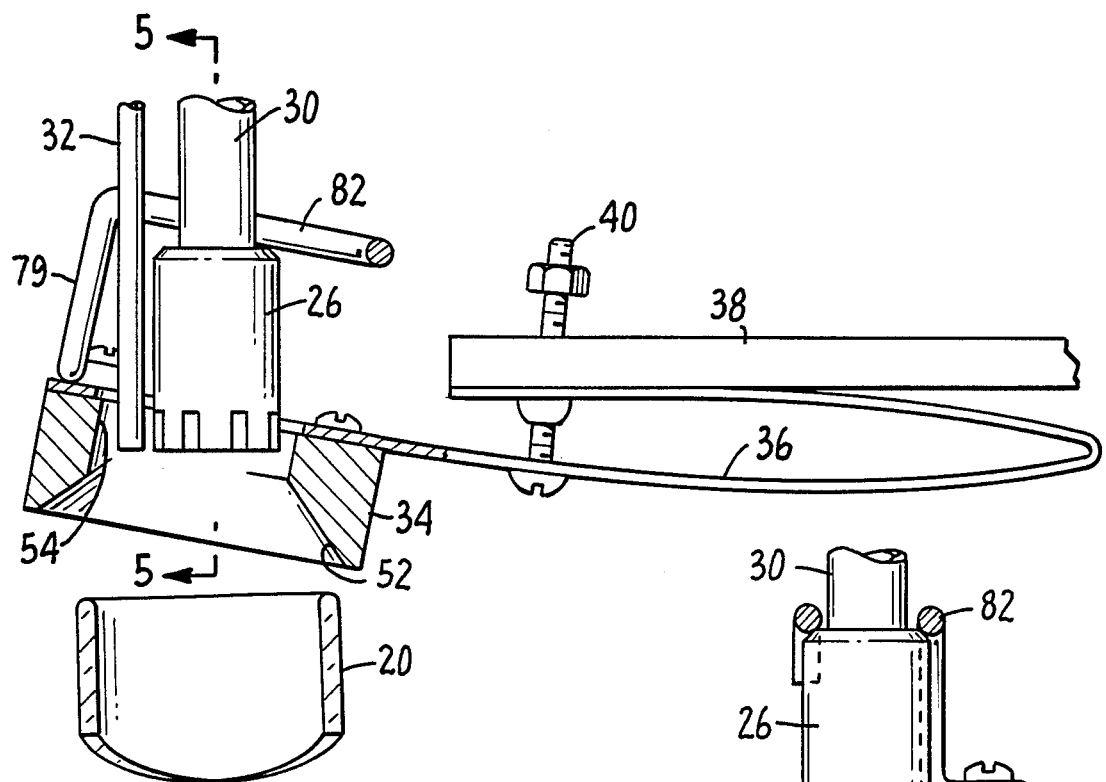
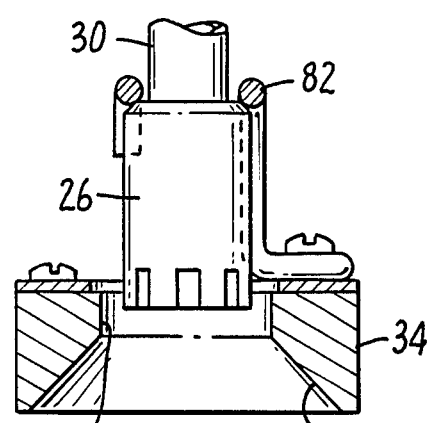
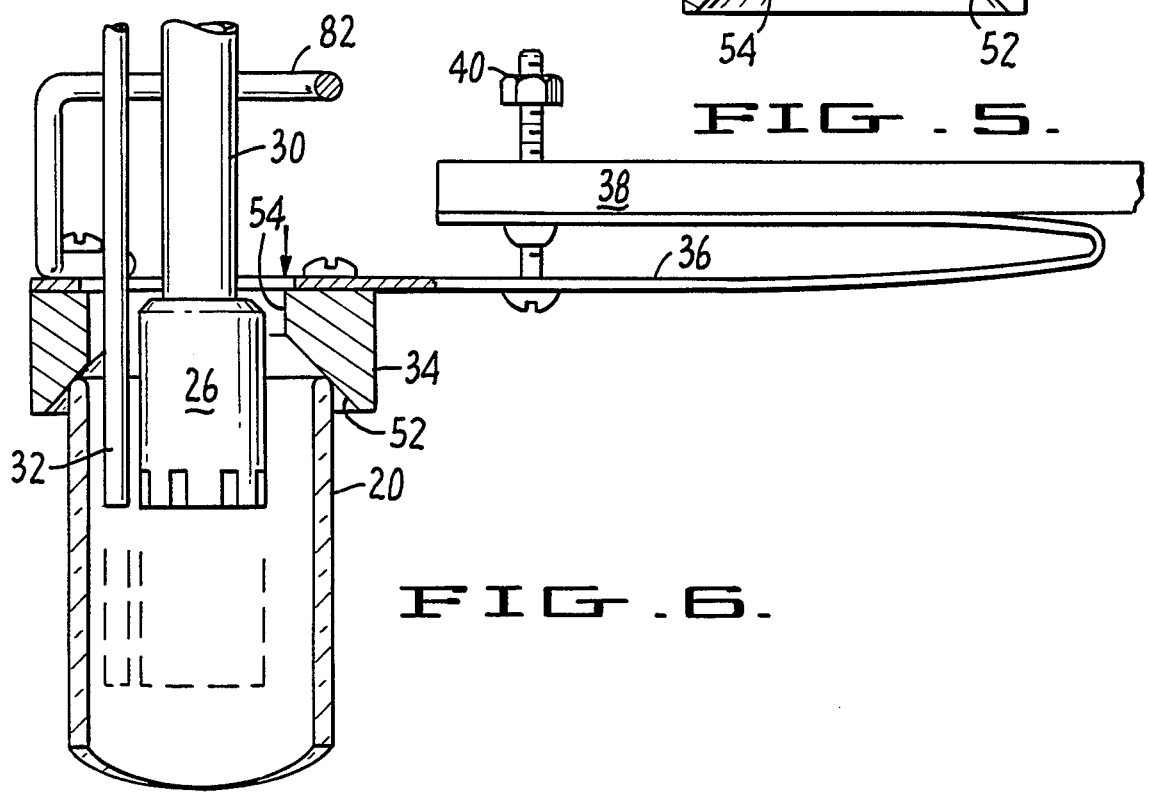

TUBE TRAP APPARATUS

DESCRIPTION

1. Technical Field

This invention relates generally to automated liquid sample analysis and the use of probes to accomplish such analyses and intermediate wash steps, and more specifically to a tube-gathering device which focuses the tube opening prior to the insertion of a wash probe into a tube containing immunoassay reagents and solid supports.

2. Background of the Invention

The automation of immunoassay techniques has spawned a series of inventions to enable efficient and reliable operation in the clinical setting. The sensitivity for detecting extremely low concentrations in immunoassay techniques requires that unreacted components of the reaction system be completely removed before the detection sequence. In practice this translates to providing washing techniques which are good to the parts per million level in cycle times compatible with clinical use. When these immunoassay techniques are practiced manually, this washing procedure could be repeated several times or each individual wash could be extended for a greater period of time. The automation of this procedure made soaking for an extended period of time impractical.

To overcome the difficulty of providing sufficient washing and drying in an automated instrument in a practical period of time, we developed a wash probe system which could accomplish a high fluid throughput in a short interval and which could vigorously inject the fluid to improve "wash" quality. The resulting probe system is of substantial diameter, approaching the diameter of the test tubes in which such assays are typically performed. The use of this probe to remove unreacted reagents is the subject of our copending applications Ser. No. 757,525 entitled METHOD AND APPARATUS FOR REMOVING UNBOUND COMPONENTS IN AUTOMATED IMMUMOASSAY TECHNIQUES, and continuation-in-part application Ser. No. 888,848, entitled METHOD AND APPARATUS FOR LIQUID ADDITION AND ASPIRATION IN AUTOMATED IMMUNOASSAY TECHNIQUES, filed on July 22, 1986, assigned to a common assignee.

While this increased probe size solved the fluid throughput problems associated with automated washing and drying procedures, the size of probe relative to the tube presented a challenge. The aspirator probe, whose horizontal position relative to a test tube is determined by two motor-driven carriages must enter a series of tubes vertically without hanging up on the edge of any tube. The test tubes are located in a rack which is not made for accuracy and it holds the tubes only loosely. Since the aspirator probe has a diameter close to that of the tube it must enter, we discovered that the probe missed the center of the tube becoming hung up on the tube top, causing failure of the instrument.

The subject invention provides a tube trap apparatus which gathers in the loosely held tube, focuses the tube rim relative to the probe and thereby permits effective and accurate insertion of the wash probe in an automated system.

It is therefore an object of this invention to provide a tube trap apparatus which permits accurate insertion of a probe whose diameter is relatively large in comparison to the receiving tube.

It is further an object of this invention to provide an inexpensive means for the use of a large wash probe which is capable of accomplishing the degree of washing and drying required in immunoassay techniques in a short period of time.

It is another object of this invention to provide a simple way to center test tubes which is effective, simple and inexpensive.

These, and further objects, shall become apparent to those skilled in the art by reference to this specification and the drawings to which it refers.

SUMMARY OF THE INVENTION

A spring is connected to a motor driven carriage which moves a probe horizontally and vertically. The restraint, which is attached to one end of the spring, is supported away from the tubes in the rack by the probe and a bail. The cooperation of the bail and the probe folds or compresses the spring when the probe is retracted. When the probe is lowered towards the mouth of a tube, the action of the spring forces the restraint down ahead of the probe. The restraint's frustoconical inner surface forces the top of the tube into a position directly in line with the probe. The probe then goes into the tube to perform the washing and drying procedures. When the probe is lifted out of the tube, the probe lifts the restraint by means of the bail. This enables the carriage and/or the tube rack to move to position the probe over the next tube.

DESCRIPTION OF THE DRAWINGS

FIG. 1 is a perspective view of the tube trap apparatus and probe of the instant invention, with partial break away.

FIG. 2 is a fragmented, perspective view of the components of the tube trap apparatus.

FIG. 3 is a top view of the tube trap apparatus and probe of the instant invention.

FIG. 4 is a cross section taken along the line 4—4 in FIG. 3.

FIG. 5 is a detailed cross section of the restraint, bail and probe, taken along the line 5—5 in FIG. 4.

FIG. 6 is a cross section taken along the line 4—4 in FIG. 3, but shows the probe inserted in the tube mouth with the spring in a relaxed, deflected position.

DETAILED DESCRIPTION OF THE INVENTION

FIG. 1 shows a test tube 20 being loosely held in a rack 22. A slot 24 is chosen to be slightly larger than the tube 20 diameter to make placement and replacement of the tube 20 easy and convenient. This freedom of movement, however, makes insertion of a probe 26 into a tube mouth 28 considerably difficult because of their relatively similar size. When the probe 26 is positioned, and made to move up or down by a shaft 30, either the probe 26 or a detergent-dispensing tube 32 can hang up on the tube mouth 28. Instead, a restraint 34, which is joined to a U-shaped spring 36, is provided to properly center the tube 20 before the probe 26 is inserted. Spring 36 is fastened to a carriage 38. A limiting bolt 40 is provided to prevent the spring 36 from deflecting too far and thus be unable to gather in a tube.

The various components of this preferred embodiment of the tube trap apparatus are shown in the fragmented view of FIG. 2. The restraint 50 is substantially rectilinear, but has a conical inner surface 52. The conical surface 52 is properly shaped to accept a tube mouth. At the apical end of the conical inner surface is a substantially round restraint aperture 54 whose size is selected to permit the probes to easily pass through it. The restraint 34 also has three apertures 56, 58 and 60 which comprise the female end of the means for affixing the restraint 50 to the spring 36. The U-shaped spring 36 is constructed of a metal which is sufficiently resilient to undergo cyclical deflection and retraction without substantial fatigue and failure. On the lower side of the spring 36 there is a substantially circular spring aperture 64 which also is sized to permit the passage of the probes. Three additional substantially circular apertures 56, 58 and 60 comprise further female ends of the means for affixing the restraint 34 to the spring 36.

A larger aperture 72 and another aperture 74 through the spring 62 are provided for the limiter which restricts the spring deflection. Apertures 76 and 78 located on the upper portion of the leaf spring 36, are provided to affix the spring 62 to the carriage (not shown in this figure) by means of screws, or the like.

A bail 79 is comprised of an eye 80, a vertical section 81 and a hook 82. The gap of the hook 82 is selected to be smaller than the diameter of the probe so that when the probe is retracted, it catches the bail hook 82 causing the spring 62 to be retracted up and away from the tube mouth. The bail 79 is held in place by a screw 84 which is placed through the eye 80 of the bail 79 and then through aperture 68 into aperture 58. A screw 86 is inserted through aperture 70 and aperture 60. A screw 88 is inserted through aperture 66 and into aperture 56. When these screws 84, 86 and 88 are tightened the restraint 50 is held tightly against the spring 62.

The way in which the bail 79, bail hook 82 and probe 26 cooperate to activate the spring 36 is shown in FIG. 3. The bail 79 is located on the top side of spring 36. The hook 82 of the bail is raised above the plane of the spring 36 by a vertical member not seen in this view. From this view it can be seen that the gap of the hook 82 is smaller than the probe 26 diameter but larger than the diameter of the shaft 30. This means that the shaft 30 and the detergent-dispensing probe 32 can freely move through the bail hook 82 in the vertical direction. The probe 26, however, is not free to move vertically through the hook 36. The effects of this restriction are more clearly illustrated in FIG. 4.

FIG. 4 shows the spring 36 in a retracted position, held up and away from the test tube mouth 28. The restraint 34 is clear of the tube 28 and the probe 26 has been extracted from the tube 28. The spring 36 is being held in the retracted position by the bail 79 which has hung up on the probe 26 as intended. The shaft 30 moved freely through the bail 79 to position the probe 26 in this "retracted" position. The carriage 38 can now move the probe 26 and restraint 34 to a new site for insertion. The limiter 40 is secured across the gap of the spring 36.

Another view of the bail-probe interaction is shown in FIG. 5. Here, it is shown that the uppermost section of the probe 26 is not free to pass through the hook of the bail 82. The probe 26 is sufficiently removed from the restraint 34 inner surface so as not to interfere with the centering process over the next tube.

The centering and insertion steps are described with reference to FIG. 6. The role of the limiter 40 is also shown. The carriage 38 has moved the probe 26 to a new position. The spring 36 begins to relax and to deflect away from the carriage 38 as the probe 26 moves out of the bail hook 82, through the restraint 34 and into the mouth 28 of the tube. The conical inner surface of the restraint 34 meets with the mouth 28 and stabilizes the tube's position relative to the probe 26 before the probe's lower end reaches the tube mouth 28. Should there arise a situation where there is no tube, but the probe 26 executes an insertion anyway, then the limiter 40 prevents the spring 36 from obtaining an extremely obtuse angle which could permanently damage the spring 36 or damage adjoining tubes, samples or the probe 26.

Although this invention has been described with reference to a particularly preferred embodiment, it will be understood by those skilled in the art that changes or modifications may be made to this embodiment which are still within the scope of the invention and the claims appended hereto.

I claim:

1. An apparatus for registering tubes with an elongate probe which comprises:
   an elongate probe selectively movable along a shaft between retracted and extended positions;
   spring means having at least one aperture therethrough for receiving said elongate probe:
   restraint means affixed to said spring means, said restraint means having an aperture therethrough which is aligned with said spring means aperture, for receiving said elongate probe, said spring means selectively biasing said restraint means against a tube top to focus a tube mouth in line with said elongate probe prior to insertion of said elongate probe into the tube mouth; and
   bail means, affixed to said spring means for receiving said elongate probe therethrough,
   wherein said elongate probe passes through said spring means aperture and said restraint means aperture and wherein said elongate probe mechanically contacts said bail means to selectively retract and to extend said restraining means relative to the tube top in sequence with said elongate probe shaft extension and retraction.

2. The apparatus of claim 1 wherein said restraint means comprises a restraint member having parallel upper and lower surfaces and a substantially frustoconical interior surface whose basal surface is substantially coincident with said restraint member lower surface and whose apex is aligned with, and communicates with, said restraint means elongate probe receiving aperture in the restraint member upper surface.

3. The apparatus of claim 1 wherein said bail means comprises an eye, a hook and a member which joins the hook and eye, said eye used to affix said bail means to the spring means, said hook being aligned with said spring means aperture to receive said elongate probe, the hook and elongate probe cooperating in direct mechanical contact to retract the restraining means from the tube mouth.

4. The apparatus of claim 1 wherein said spring means is a U-shaped leafspring.

5. The apparatus of claim 4 wherein said spring means further comprises a nut and bolt extending through said U-shaped leafspring for limiting the deflection of said U-shaped leafspring.

6. The apparatus of claim 4 wherein said spring means further comprises a cross bar means to limit the deflection of the U-shaped leafspring.

7. An apparatus for registering tubes with an elongate probe which comprises:
- an elongate probe selectively movable along a shaft between retracted and extended positions;
- a U-shaped spring having an aperture therethrough for receiving said elongate probe;
- a hollow, substantially frustoconical restraining member, affixed to said U-shaped spring, whose basal face cooperates with a tube top to focus a tube mouth along the longitudinal axis of said elongate probe to enable insertion of the elongate probe into the tube mouth in said elongate probe's extended position, said restraining member permitting said elongate probe to pass freely therethrough; and, a bail means which is affixed to said spring means for receiving said elongate probe and cooperating therewith by direct mechanical contact to retract said restraining member from resting upon the tube top as said elongate probe moves away from the tube top and toward its retracted position.

8. A probe accepting, tube focussing apparatus which comprises:
- a bail member having an eye and a probe-receiving half loop offset from said eye by a vertical member;
- a U-shaped leaf spring having two arms of unequal length and a probe-receiving aperture through the longer of the two leaf spring arms; and,
- a restraint member having parallel upper and lower surfaces and a frustoconical interior surface whose apex aligns with, and communicates with, a probe receiving aperture in the restraint member upper surface and whose basal surface is substantially coincident with said restraint member lower surface;
- wherein said bail member is fastened to an upper surface of said U-shaped leaf spring longer arm by said eye and said half loop is aligned with said U-shaped leaf spring probe-receiving aperture and wherein said restraint member upper surface is fastened to a lower surface of the leaf spring longer arm to align said restraint member probe receiving aperture with said leaf spring probe receiving aperture.

9. A probe, subtended from a support by a shaft, said probe selectively extended and retracted relative to said support by said shaft, said probe having an enlarged end member,
in combination with:
- a restraint member having an aperture therethrough which is sufficiently large to permit said enlarged probe end to pass freely therethrough; and,
- a bail means, affixed to said restraint member aperture, having a half loop disposed about said restraint member aperture, said loop having an inner diameter which is smaller in magnitude than an outer diameter of said enlarged end member, said loop inner diameter being large than an outer diameter of said shaft, thereby permitting said probe shaft to pass freely through said bail half loop while said probe enlarged end member is not permitted to pass through said half loop.

* * * * *